United States Patent [19]
Gelboin et al.

[11] Patent Number: 6,060,253
[45] Date of Patent: May 9, 2000

[54] AGENTS THAT BIND TO AND INHIBIT HUMAN CYTOCHROME P450 2D6

[75] Inventors: Harry V. Gelboin, Chevy Chase; Frank J. Gonzalez, Bethesda; Kristopher W. Krausz, Columbia, all of Md.

[73] Assignee: The United States of America as represented by the Department of Health and Human Services, Washington, D.C.

[21] Appl. No.: 08/788,599

[22] Filed: Jan. 23, 1997

[51] Int. Cl.⁷ .................. G01N 33/573; G01N 33/577; C07K 16/40; C12N 15/06
[52] U.S. Cl. ................. 435/7.1; 530/388.26; 530/387.1; 530/388.15; 435/338; 435/252.1
[58] Field of Search ............................ 530/387.1, 387.3, 530/387.7, 388.15, 388.26; 435/4, 338, 252.1, 7.1, 25, 40.5, 40.51, 40.52; 436/501, 503

[56] References Cited

U.S. PATENT DOCUMENTS 5,508,199  4/1996  Gonzalez et al. .

OTHER PUBLICATIONS

Elaine Buchert et al., "Clinical Implications of Variable Antiarrhythmic Drug Metabolism", (1992) *Pharmacogenetics*, vol. 2, pp. 2–11.
Cribb et al., "Antipeptide Antibodies Against Overlapping Sequences Differentially Inhibit Human CYP2D6", (1995) *Drug Metabolism & Disposition*, vol. 23, No. 7, pp. 671–675.
Marja–Liisa Dahl et al., "Genetically Variable Metabolism of Antidepressants and Neuroleptic Drugs in Man", (1993) *Pharmacogenetics*, vol. 3, pp. 61–70.
S. Wynn Ellis et al., "Catalytic Activities of Human Debrisoquine 4–Hydroxylase Cytochrome P450 (CYP2D6) Expressed in Yeast", (1992) *Biochemical Pharmacology*, vol. 44, No. 4, pp. 617–620.
Harry V. Gelboin et al., "Inhibitory and Non–Inhibitory Monoclonal Antibodies to Human Cytochrome P450 3A3/4", (1995) *Biochemical Pharmacology*, vol. 50., No. 11, pp. 1841–1850.
Harry V. Gelboin, "Cytochrome P450 and Monoclonal Antibodies", (1993) *Pharmacological Reviews*, vol. 45, No. 4, pp. 413–453.
Harry V. Gelboin et al., "Inhibitory and Noninhibitory Monoclonal Antibodies to Human Cytochrome P450 2E1" (1996) *Chemical Research in Toxicology*, vol. 9. No. 6, pp. 1023–1030.
Elizabeth M.J. Gilliam et al., "Expression of Cytochrome P450 2D6 in *Escherichia Coli*, Purification, and Spectral and Catalytic Characterization", (Jun. 1, 1995) *Archieves of Biochemistry and Biophysics*, vol. 319, No. 2, pp. 540–550.
Frank J. Gonzalez et al., "Role of Human Cytochrome P–450s in Risk Assessment and Susceptibility to Environmentally Based Disease", (1993) *Journal of Toxicology and Environmental Health*, vol. 40, pp. 289–308.

Frank J. Gonzalez et al., "Pharmacogenetic Phenotyping and Genotyping, Present Status and Future Potential" (1994) *Clin. Pharmacokinet.*, vol. 26. No. 1, pp. 59–70.
Frank J. Gonzalez et al., "Human Debrisoquine 4–Hydroxylase (P450LLD1): cDNA and Deduced Amino Acid Sequence and Assignment of the CYP2D Locus to Chromosome 22", (1988) *Genomics*, vol. 2, pp. 174–179.
Frank J. Gonzalez et al., "Expression of Mammalian Cytochrome P450 Using Baculovirus", (1991) *Methods in Enzymology*, vol. 206, pp. 93–99.
F.J. Gonzalez et al., "Characterization of the Common Genetic Defect in Humans Deficient in Debrisoquine Metabolism", (Feb. 4, 1988) *Nature*, vol. 331, No. 6155, pp. 442–446.
Grogan, James et al., "Cytochrome P450 2A1, 2E1, and 2C9 cDNA–Expression By Insect Cells and Partial Purification Using Hydrophobic Chromatography", (1995) *Biochemical Pharmacology*, vol. 50, No. 9, pp. 1509–1515.
Kristopher W. Krausz et al., "The Production of Inhibitory and Immunoblotting Monoclonal Antibodies to Human Cytochrome P450 2D6", American Society for Pharmacology and Experimental Therapeutics Annual Meeting, San Diego, California, (Mar. 7–11, 1997) 1 page.
T. Kronbach, "Bufuralol, Dextromethorphan, and Debrisoquine As Prototype Substrates for Human P450 2D6", (1991) *Methods in Enzymology*, vol. 206, pp. 509–517.
Thomayant Prueksaritanont et al., "(+)–Bufuralol 1'–Hydroxylation Activity in Human and Rhesus Monkey Intestine and Liver", (1995) *Biochemical Pharmacology*, vol. 50, No. 9, pp. 1521–1525.
C. Transon et al., "Interindividual Variability in Catalytic Activity and Immunoreactivity of Three Major Human Liver Cytochrome P450 Isozymes", (1996) *Eur. J. Clin. Pharmacol.* vol. 51, pp. 79–85.
Hiroshi Yamazaki et al., "Bufuralol Hydroxylation by Cytochrome P450 2D6 and 1A2 Enzymes in Human Liver Microsomes", (1994) *Molecular Pharmacology*, vol. 46, pp. 568–577.
Ulrich M. Zanger et al., "Antibodies Against Human Cytochrome P–450db1 in Autoimmune Hepatitis Type II", (1988) *Proc. Natl. Acad. Sci. USA*, vol. 85, pp. 8256–8260.

*Primary Examiner*—Paula K. Hutzell
*Assistant Examiner*—Anne L. Holleran
*Attorney, Agent, or Firm*—Townsend & Townsend & Crew

[57] ABSTRACT

The invention provides monoclonal antibodies and other binding agents to human cytochrome P450 2D6 having advantageous properties, including capacity substantially to inhibit enzyme activity of human cytochrome P450 2D6 and lack of specific binding to other human cytochromes P450. The binding agents of the invention are useful in methods for screening drugs for metabolism by cytochrome P450 2D6, and in methods of screening individuals for a poor metabolizing human P450 2D6 phenotype.

22 Claims, 3 Drawing Sheets

AGENTS THAT BIND TO AND INHIBIT HUMAN CYTOCHROME P450 2D6

TECHNICAL FIELD

The present invention resides in the technical fields of immunology and enzymology.

BACKGROUND OF THE PRESENT INVENTION

The cytochrome P450 family of enzymes is primarily responsible for the metabolism of xenobiotics such as drugs, carcinogens and environmental chemicals, as well as several classes of endobiotics such as steroids and prostaglandins. Members of the cytochrome P450 family are present in varying levels and their expression and activities are controlled by variables such as chemical environment, sex, developmental stage, nutrition and age.

More than 200 cytochrome P450 genes have been identified. There are multiple forms of these P450 and each of the individual forms exhibit degrees of specificity towards individual chemicals in the above classes of compounds. In some cases, a substrate, whether it be drug or carcinogen, is metabolized by more then one of the cytochromes P450. Genetic polymorphisms of cytochromes P450 result in phenotypically-distinct subpopulations that differ in their ability to perform biotransformations of particular drugs and other chemical compounds.

These phenotypic distinctions have important implications for selection of drugs. For example, a drug that is safe when administered to most humans may cause toxic side-effects in an individual suffering from a defect in an enzyme required for detoxification of the drug. Alternatively, a drug that is effective in most humans may be ineffective in a particular subpopulation because of lack of a enzyme required for conversion of the drug to a metabolically active form. Further, individuals lacking a biotransformation enzyme are often susceptible to cancers from environmental chemicals due to inability to detoxify the chemicals. Eichelbaum et al., *Toxicology Letters* 64165, 155–122 (1992). Accordingly, it is important to identify individuals who are deficient in a particular P450 enzyme, so that drugs known or suspected of being metabolized by the enzyme are not used, or used only with special precautions (e.g., reduced dosage, close monitoring) in such individuals. Identification of such individuals may indicate that such individuals be monitored for the onset of cancers.

Cytochrome P450 2D6, also known as debrisoquine hydroxylase, is the best characterized polymorphic P450 in the human population (Gonzalez et al., *Nature* 331:442–446 (1988)). A poor metabolizer phenotype has been reported which behaves as an autosomat recessive trait with an incidence between 5 and 10% in the white population of North America and Europe. Poor metabolizers exhibit negligible amounts of cytochrome P450 2D6 (Gonzales et al., supra). Genetic differences in cytochrome P450 2D6 may be associated with increased risk of developing environmental and occupational based diseases. See Gonzalez & Gelboin, *J. Toxicology and Environmental Health* 40, 289–308 (1993)).

Several drugs for treating cardiovascular and psychiatric disorders are known substrates of cytochrome P450 2D6. (Dahl and Bertilsson, *Pharmacogenetics* 3, 61–70 (1993)), a situation that creates problems in prescribing such drugs. Although such drugs may be the most effective treatment for most of the population, physicians are reluctant to prescribe them due to the risk of adverse effects in poor metabolizers. Buchert et al., *Pharmacogenetics* 2, 2–11 (1992); Dahl et al., *Pharmacogenetics* 3, 61–70 (1993).

Existing methods of identifying deficiencies in patients are not entirely satisfactory. Patient metabolic profiles are currently assessed with a bioassay after a probe drug administration. For example, a poor drug metabolizer with a 2D6 defect is identified by administering one of the probe drugs, debrisoquine, sparteine or dextromethorphan, then testing urine for the ratio of unmodified to modified drug. Poor metabolizers (PM) exhibit physiologic accumulation of unmodified drug and have a high metabolic ratio of probe drug to metabolite. This bioassay has a number of limitations: lack of patient cooperation, adverse reactions to probe drugs, and inaccuracy due to coadministration of other pharmacological agents or disease effects. See, e.g., Gonzalez et al., *Clin. Pharmacokin.* 26, 59–70 (1994). Genetic assays by RFLP (restriction fragment length polymorphism), ASO PCR (allele specific oligonucleotide hybridization to PCR products or PCR using mutant/wildtype specific oligo primers), SSCP (single stranded conformation polymorphism) and TGGE/DGGE (temperature or denaturing gradient gel electrophoresis), MDE (mutation detection electrophoresis) are time-consuming, technically demanding and limited in the number of gene mutation sites that can be tested at one time.

A serious complication in patient drug choice is that most drugs have not been characterized for their metabolism by P450 2D6 and other cytochromes P450. Without knowing which cytochrome(s) p450 is/are responsible for metabolizing an individual drug, an assessment cannot be made for the adequacy of a patient's P450 profile. For such drugs, there is a risk of adverse effects if the drugs are administered to poor metabolizers.

Possible roles of monoclonal antibodies in cytochrome P450 research including detection, immunolocalization, immunopurification and phenotyping of particular cytochrome P450 isozymes are reviewed by Gelboin, *Pharmacological Reviews* 45, 413–453 (1993). Cribb et al., *Drug Metabolism & Disposition* 23, 671–675 (1995) discuss polyclonal antibodies raised against two peptides that correspond to a 33 amino acid sequence of cytochrome P450 2D6. They report that antisera raised against a peptide corresponding to amino acids 254–273 inhibited up to 95% of dextromethorphan Odemethylase activity in human liver microsomes but lacked crossreactivity with recombinant cytochromes P450 1A2, 2C9, 2E1, or 3A4. Gonzalez et al., (1988), supra report that a rat polyclonal antibody to P450 2D6 enzyme inhibited human liver microsomal bufuralol F-hydroxylase, and human purified 2D6 protein in an in vitro reconstituted enzyme assay. Prueksaritanont et al., *Biochemical Pharmacology* 50, 1521–1525 (1995) report a polyclonal P450 2D6 antibody raised against a 20 amino acid peptide containing residues 243–273 of the native protein. The polyclonal antibody was used to compare (+)-bufuralol F-hydroxylation in human and rhesus monkey intestinal microsomes with hepatic microsomes. It was reported that the polyclonal anti-cytochrome P450 2D6 antibody inhibited bufuralol metabolism in human liver by about 75%. Certain mouse monoclonal antibodies to human cytochrome P450 2D6 are discussed by Transon et al., *Eur. J. Clin. Pharmacol.* 51, 79–85 (1996) and Willis et al., *Biochemical Pharmacol.*, 44, 617–620 (1992). Transon et al. note that different antibodies to 2D6 vary greatly in properties. None of the monoclonals discussed by Transon et al. or Willis et al. are reported to inhibit 2D6 activity.

The present invention provides inter alia monoclonal antibodies that specifically bind to human cytochrome P450

2D6 and inhibit its activity. The monoclonal antibodies can be used to screen drugs for their metabolism by 2D6 and/or identify 2D6 poor metabolizers by simple bioassays, thereby overcoming the problems in prior complicated methods discussed above.

SUMMARY OF THE CLAIMED INVENTION

The invention provides monoclonal antibodies and other binding agents to human cytochrome P450 2D6 having advantageous properties. The epitope specificity of binding agents is defined by their capacity to compete with one of three monoclonal antibodies selected from the group consisting of Mab 512-1-8 (ATCC HB-12266), MAb 50-1-3 (ATCC HB-12267), and MAb 4-74-1 (ATCC HB-12268) for specific binding to human cytochrome p450 2D6. Advantageous properties of preferred binding agents of the invention include capacity to inhibit enzyme activity of human cytochrome P450 2D6, and lack of specific binding to at least one cytochrome P450 selected from the group consisting of human cytochromes P450 1A2, 2C8, 2C9, 3A4, 3A5, 2B6, and 2E1.

In a second embodiment, the invention provides cell lines producing the monoclonal antibodies described above. The cell lines can be procaryotic or eucaryotic.

In a third embodiment, the invention provides methods of determining whether cytochrome P450 2D6 metabolizes a compound. Such a method entails contacting the compound with cytochrome P450 2D6 in the presence of varying amounts of a binding agent of the invention. Metabolism of the compound is then assayed as a function of amount of binding agent. A decrease of metabolism with amount of binding agent indicates that cytochrome P450 2D6 metabolizes the compound.

In a fourth embodiment, the invention provides methods of detecting cytochrome p450 2D6. Such a method entails contacting a sample suspected of containing cytochrome P450 2D6 with a binding agent of the invention. One then determines whether the agent specifically binds to the sample. Specific binding indicates the presence of cytochrome P450 2D6 in the sample.

In a fifth embodiment, the invention provides methods of diagnosing a poor metabolizing phenotype in an individual. Such a method entails preparing a reaction mixture comprising a tissue sample from the individual, a substrate of 2D6, and varying amounts of a binding agent of the invention. The reaction conditions are such that the substrate would be metabolized if no binding agent were present and the individual has a normal metabolizing 2D6 phenotype. One then determines metabolism of the compound in the reaction mixture as a function of the amount of agent. A lack of correlation between metabolism and amount of agent indicates a poor metabolizing 2D6 phenotype in the individual.

DEFINITIONS

Specific binding between an antibody or other binding agent and an antigen means a binding affinity of at least $10^6$ $M^{-1}$. Preferred binding agents bind human cytochrome P450 2D6 with affinities of at least about $10^7$ $M^{-1}$, and preferably $10^8$ $M^{-1}$ to $10^9$ $M^{-1}$ or $10^{10}$ $M^{-1}$.

The term epitope means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

Amino acids from the variable regions of the mature heavy and light chains of immunoglobulins are designated Hx and Lx respectively, where x is a number designating the position of an amino acids according to the scheme of Kabat et al., *Sequences of Proteins of Immunological Interest* (National Institutes of Health, Bethesda, Md. (1987) and (1991)) Kabat et al. list many amino acid sequences for antibodies for each subclass, and list the most commonly occurring amino acid for each residue position in that subclass. Kabat et al. use a method for assigning a residue number to each -amino acid in a listed sequence, and this method for assigning residue numbers has become standard in the field. Kabat et al.'s scheme is extendible to other antibodies not included in the compendium by aligning the antibody in question with one of the consensus sequences in Kabat et al. The use of the Kabat et al. numbering system readily identifies amino acids at equivalent positions in different antibodies. For example, an amino acid at the L50 position of a human antibody occupies the equivalence position to an amino acid position L50 of a mouse antibody.

The term antibody is used to mean whole antibodies and binding fragments thereof.

Sequence identity between an antibody variable domain chain and a correspondence reference antibody chain is determined when the polypeptides are optimally aligned by programs such as BLAZE (Intelligenetics) GAP or BESTFIT, using default gap weights. Preferred antibody chains share at least 70 percent or 85 percent sequence identity with the reference chain, preferably at least 90 percent sequence identity, more preferably at least 95 or 99 percent sequence identity. Preferably, residue positions which are not identical differ by conservative amino acid substitutions.

An isolated species means an object species (e.g., a binding polypeptide of the invention) that is the predominant species present (i.e., on a molar basis it is more abundant than any other individual species in the composition). Preferably, an isolated species comprises at least about 50, 80 or 90 percent (on a molar basis) of all macromolecular species present. Most preferably, the object species is purified to essential homogeneity (contaminant species cannot be detected in the composition by conventional detection methods).

DETAILED DESCRIPTION OF THE PRESENT INVENTION

The invention provides monoclonal antibodies and other binding agents in isolated form that specifically bind to human cytochrome P450 2D6. Preferred agents inhibit enzymic activity of 2D6 and lack specific binding to other human cytochromes P450. The invention further provides methods of using the antibodies and other binding agents in identifying individuals with a poor metabolizing 2D6 phenotype, and in screening drugs for metabolism by cytochrome P450 2D6.

I. Binding Agents of the Invention

A. Specificity and Functional Properties

Binding agents of the invention compete with exemplary antibodies designated Mab 512-1-8 (ATCC HB-12266), MAb 50-1-3 (ATCC HB-12267), and MAb 4-74-1 (ATCC HB-12268) for specific binding to human cytochrome P450 2D6. Production of monoclonal antibodies Mab 512-1-8, MAb 50-1-3, and MAb 4-74-1 is described in the Examples.

Mab 512-1-8 and Mab 50-1-3 are preferred agents of the invention by virtue of their capacity to inhibit enzymic activity of cytochrome 2D6. The data in the Examples show that out of the total repertoire of antibodies to human cytochrome P450 2D6, only a small proportion inhibit 2D6 enzymic activity. Binding agents that compete with Mab 512-1-8 or Mab 50-1-3 for binding to cytochrome P450 2D6 are expected to share similar inhibitory properties because inhibition by 512-1-8 or Mab 50-1-3 likely arises through binding to an active site of 2D6, and competing agents bind to the same or closely proximate site as Mab 512-1-8 or Mab 50-1-3. Capacity to compete with Mab 512-1-8 and Mab 50-1-3 thus defines a select subclass of antibodies with advantageous properties from the total repertoire of antibodies to human cytochrome P450 2D6.

The three reference antibodies for the competition assay, Mab 512-1-8, MAb 50-1-3, and MAb 4-74-1 show different functional properties indicating that binding of these antibodies likely defines three distinct epitopes on human cytochrome P450. MAb 512-1-8 shows strong inhibition of 2D6 enzymic activity and binds to human 2D6 on an immunoblot indicating it binds to an epitope important to enzymic activity that is not lost on treatment with a denaturing solvent. MAb 50-1-3 strongly inhibits enzymic activity but does not bind under immunoblot, suggesting the enzyme recognizes an epitope important to enzymic activity which is lost on treatment with a denaturing solvent. Finally, MAb 4-74-1 does not inhibit enzymic activity but does bind human 2D6 by immunoblot, suggesting that it binds to an epitope that is not involved in catalytic activity and is retained after treatment with a denaturing solvent.

Hybridomas producing Mab 512-1-8 (ATCC HB-12266), MAb 50-1-3 (ATCC HB-12267), and MAb 4-74-1 (ATCC Hb-12268) have been deposited with the American Type Culture Collection, 10801 University Boulevard, Manassas, Va. 20110-2209 on Jan. 21, 1997 under the Budapest Treaty and given the Accession Nos. indicated. These cell lines will be maintained at an authorized depository and replaced in the event of mutation, nonviability or destruction for a period of at least five years after the most recent request for release of a sample was received by the depository, for a period of at least thirty years after the date of the deposit, or during the enforceable life of the related patent, whichever period is longest. All restrictions on the availability to the public of these cell lines will be irrevocably removed upon the issuance of a patent from the application.

Competition is determined by an assay in which the antibody under test inhibits specific binding of a reference antibody to an antigenic determinant on human cytochrome P450 2D6. Numerous types of competitive binding assays are known for example: (see Harlow and Lane, "Antibodies, A Laboratory Manual," Cold Spring Harbor Press (1988)). Typically, such an assay involves the use of purified human cytochrome P450 206, an unlabelled test antibody and a labelled reference antibody. Competitive inhibition is measured by determining the amount of label bound to human cytochrome P450 2D6 in the presence of the test antibody. Usually the test antibody is present in excess. Antibodies identified by competition assay (competing antibodies) include antibodies binding to the same epitope as a reference antibody and antibodies binding to an adjacent epitope sufficiently proximal to the epitope bound by the reference antibody for steric hindrance to occur. Usually, when a competing antibody is present in excess, it will inhibit specific binding of a reference antibody to human cytochrome P450 2D6 by at least 10, 25, 50 or 75%.

Binding agents of the invention typically lack specific binding (i.e., crossreactivity) to human cytochromes P450 other than 2D6, so that the binding agents can be used to detect human cytochrome P450 2D6 in the presence of other cytochromes P450. For example, binding agents of the invention typically lack specific binding to one or more of human cytochromes P450 1A2, 2C8, 2C9, 3A4, 3A5, 2B6 and 2E1. Some binding agents of the invention, including the exemplified Mab 512-1-8, MAb 50-1-3, and MAb 4-74-1, lack specific binding to all of the above human cytochromes P450.

As noted above, preferred binding agents of the invention are further characterized by capacity to inhibit human cytochrome P450 2D6catalyzed metabolism of a substrate known to be metabolized by the enzyme. The enzyme is generally assayed with bufurolol as a substrate (Kronbach et al., *Anal. Biochem.* 162, 24–32 (1987); *Methods Enzymol.* 206, 509–517(1991) (see present Examples). Assays can be performed in either a microsome systems or a reconstituted systems of purified enzymes. For example, a suitable microsome system contains I mg/ml protein of human liver microsomes or 1.6 mg protein/ml from human lymphoblast cell lines, 0.4 mM bufurolol in a final volume of 0.10 ml of 100 mM potassium phosphate buffer, pH 7.5 containing an NADPH generating system. An exemplary reconstituted system contains about 20–50 nM purified human P450 2D6, 40–100 nM cytochrome b5, 100 nM NADPH-P450 reductase, 10 /µg/ml phospholipids and 0.25 mM sodium cholate. Incubations are typically carried out at 37° C. for 30 min. Percentage inhibition is defined as 1—(rate of formation metabolic product in presence of test antibody/rate of formation of metabolic product in presence of control antibody), when antibody is present in excess. (The control antibody is an antibody lacking specific binding to human cytochrome P450 2D6.) Some agents of the invention inhibit metabolic capacity of isolated pure cytochrome P450 2D6 on bufurolol by at least 25%, 50%, 75%, 90% or 95%. Alternative assays using the substrate dextromethorphan, desbrisoquine or sparteine can also be used. See, e.g., Transon et al., *Eur. J. Clin. Pharmacol.* 51, 79–85 (1996).

B. Antibodies of the Invention

1. General Characteristics

The basic antibody structural unit is known to comprise a tetramer. Each tetramer is composed of two identical pairs of polypeptide chains, each pair having one "light" (about 25 kDa) and one "heavy" chain (about 50–70 kDa). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See generally, *Fundamental Immunology* (Paul, W., ed., 2nd ed. Raven Press, N.Y., 1989), Ch. 7 (incorporated by reference in its entirety for all purposes).

The variable regions of each light/heavy chain pair form the antibody binding site. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. CDR and FR residues are delineated according to the standard sequence definition of Kabat et al., supra. An alternative structural definition has been proposed by Chothia et al., *J. Mol. Biol.* 196, 901–917 (1987); *Nature* 342, 878–883 (1989); and *J. Mol. Biol.* 186, 651–663 (1989).

2. Production

Antibodies to human cytochrome P450 2D6 can be produced by a variety of means. The production of non-human monoclonal antibodies, e.g., murine or rat, can be accomplished by, for example, immunizing the animal with a preparation containing purified human cytochrome P450 or a fragment thereof. The immunogen can be obtained from a natural source, by peptides synthesis or preferably by recombinant expression. Antibody-producing cells obtained from the immunized animals are immortalized and screened for the production of an antibody which binds to human cytochrome P450 or a fragment thereof. See Harlow & Lane, *Antibodies, A Laboratory Manual* (CSHP NY, 1988) (incorporated by reference for all purposes).

Humanized forms of mouse antibodies can be generated by linking the CDR regions of non-human antibodies to human constant regions by recombinant DNA techniques. See Queen et al., *Proc. Natl. Acad. Sci. USA* 86, 10029–10033 (1989) and WO 90/07861 (incorporated by reference for all purposes).

Human antibodies can be obtained using phage-display methods. See, e.g., Dower et al., WO 91/17271; McCafferty et al., WO 92/01047. In these methods, libraries of phage are produced in which members display different antibodies on their outersurfaces. Antibodies are usually displayed as Fv or Fab fragments. Phage displaying antibodies with a desired specificity are selected by affinity enrichment to human cytochrome P450 or a fragment thereof. Human antibodies are selected by competitive binding experiments, or otherwise, to have the same epitope specificity as a particular mouse antibody, such as Mab 512-1-8, MAb 50-1-3, and MAb 4-74-1. Such antibodies are particularly likely to share the useful functional properties of the exemplified antibodies.

3. Antibody Fragments

The invention further provides fragments of the intact antibodies described above. Typically, these fragments compete with the intact antibody from which they were derived for specific binding to human cytochrome P450 2D6, and bind with an affinity of at least $10^6$, $10^7$, $10^{8,}$ $10^9$ $M^{-1}$, or $10^{10}$ $M^{-1}$. Antibody fragments include separate heavy chains, light chains Fab, Fab' F(ab')$_2$, Fv, and single chain antibodies comprises a heavy chain variable region linked to a light chain variable region via a peptide spacer. Fragments can be produced by enzymic or chemical separation of intact immunoglobulins. For example, a F(ab')$_2$ fragment can be obtained from an IgG molecule by proteolytic digestion with pepsin at pH 3.0–3.5 using standard methods such as those described in Harlow and Lane, supra. Fab fragments may be obtained from F(ab')$_2$ fragments by limited reduction, or from whole antibody by digestion with papain in the presence of reducing agents. (See id.) Fragments can also be produced by recombinant DNA techniques. Segments of nucleic acids encoding selected fragments are produced by digestion of full-length coding sequences with restriction enzymes, or by de novo synthesis. Often fragments are expressed in the form of phage-coat fusion proteins. This manner of expression is advantageous for affinity-sharpening of antibodies.

4. Recombinant Expression of Antibodies

Nucleic acids encoding light and heavy chain variable regions, optionally linked to constant regions, are inserted into expression vectors. The light and heavy chains can be cloned in the same or different expression vectors. The DNA segments encoding antibody chains are operably linked to control sequences in the expression vector(s) that ensure the expression of antibody chains. Such control sequences include a signal sequence, a promoter, an enhancer, and a transcription termination sequence. Expression vectors are typically replicable in the host organisms either as episomes or as an integral part of the host chromosome.

*E. coli* is one procaryotic host particularly for expressing antibodies of the present invention. Other microbial hosts suitable for use include bacilli, such as *Bacillus subtilus,* and other enterobacteriaceae, such as Salmonella, Serratia, and various Pseudomonas species. In these prokaryotic hosts, one can also make expression vectors, which typically contain expression control sequences compatible with the host cell (e.g., an origin of replication) and regulatory sequences such as a lactose promoter stem, a tryptophan (trp) promoter system, a beta-lactamase promoter * system, or a promoter system from phage lambda.

Other microbes, such as yeast, may also be used for expression. Saccharomyces is a preferred host, with suitable vectors having expression control sequences, such as promoters, including 35 phosphoglycerate kinase or other glycolytic enzymes, and an origin of replication, termination sequences and the like as desired.

Mammalian tissue cell culture can also be used to express and produce the antibodies of the present invention (see Winnacker, *From Genes to Clones* (VCH Publishers, N.Y., 1987). Eukaryotic cells are preferred, because a number of suitable host cell lines capable of secreting intact antibodies have been developed. Preferred suitable host cells for expressing nucleic acids encoding the immunoglobulins of the invention include: monkey kidney CVI line transformed by SV40 (COS-7, ATCC CRL 1651); human embryonic kidney line (293) (Graham et al., *J. Gen. Virol.* 36:59 (1977)); baby hamster kidney cells (BHK, ATCC CCL 10); Chinese hamster ovary-cells-DHFR (CHO, Urlaub and Chasin, *Proc. Natl. Acad. Sci. (USA)* 77:4216 (1980)); mouse sertoli cells (TM4, Mather, *Biol. Reprod.* 23:243–251 (1980)); monkey kidney cells (CV1 ATCC CCL 70); african green monkey kidney cells (VERO-76, ATCC CRL 1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); and, TRI cells (Mather et al., *Annals N.Y. Acad. Sci.* 383:4446 (1982)); baculovirus cells.

The vectors containing the polynucleotide sequences of interest (e.g., the heavy and light chain encoding sequences and expression control sequences) can be transferred into the host cell. Calcium chloride transfection is commonly utilized for prokaryotic cells, whereas calcium phosphate treatment or electroporation can be used for other cellular hosts. (See generally Sambrook et al., *Molecular Cloning: A Laboratory Manual* (Cold Spring Harbor Press, 2nd ed., 1989) (incorporated by reference in its entirety for all purposes). When heavy and light chains are cloned on separate expression vectors, the vectors are co-transfected to obtain expression and assembly of intact immunoglobulins. After introduction of recombinant DNA, cell lines expressing immunoglobulin products are cell selected. Cell lines capable of stable expression are preferred (i.e., undiminished levels of expression after fifty passages of the cell line).

Once expressed, the whole antibodies, their dimers, individual light and heavy chains, or other immunoglobulin forms of the present invention can be purified according to standard procedures of the art, including ammonium sulfate precipitation, affinity columns, column chromatography, gel electrophoresis and the like (see generally Scopes, *Protein Purification* (Springer-Verlag, N.Y., 1982). Substantially pure immunoglobulins of at least about 90 to 95% homogeneity are preferred, and 98 to 99% or more homogeneity most preferred.

5. Screening for Sequence Analogs

Many of the antibodies described above can undergo non-critical amino-acid substitutions, additions or deletions in both the variable and constant regions without loss of binding specificity or effector functions, or intolerable reduction of binding affinity (i.e., below about $10^6$ $M^{-1}$) for human cytochrome P450 2D6. Usually, the light and heavy chain variable regions of immunoglobulins incorporating such alterations exhibit at least 80, 90 or 95% sequence identity to the corresponding regions of a reference immunoglobulin from which they were derived, such as Mab 512-1-8, MAb 50-1-3, and MAb 4-74-1. Preferred antibody light and heavy chain sequence variants have the same complementarity determining regions (CDRs) as the corresponding chains from one of the above reference antibodies. Occasionally, a mutated immunoglobulin can be selected having the same specificity and increased affinity compared with a reference immunoglobulin from which it was derived. Phage-display technology offers powerful techniques for selecting such immunoglobulins. See, e.g., Dower et al., WO 91/17271 McCafferty et al., WO 92/01047; Huse, WO 92/06204.

C. Other Binding Agents of the Invention

The invention further provides nonantibody binding agents that compete with one of the exemplified antibodies for binding to human cytochrome P450 2D6. These binding agents include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of Ad the compounds can be constructed by the encoded synthetic libraries (ESL) A method described in Affymax, WO 95/12608, Affymax, WO 93/06121, Columbia University, WO 94/08051, Pharmacopeia, WO 95/35503 and Scripps, WO 95/30642 (each of which is incorporated by reference for all purposes). Peptide libraries can also be generated by phage display methods. See, e.g., Devlin, WO 91/18980. The libraries of compounds are screened for binding to human cytochrome P450 in competition with one of the reference antibodies Mab 512-1-8, MAb 50-1-3, and MAb 4-74-1.

II. Human Cytochrome P450 2D6

The cDNA for human cytochrome P450 2D6 has been cloned, sequenced, and expressed in Cos cells (Gonzalez et al., *Nature* 331, 442–446 (1988)); U.S. Pat. No. 5,508,199. Sources of other cytochromes P450 (e.g., for use in testing for lack of crossreactivity) are described by Nebert, *DNA & Cell Biol.* 10, 1–14 (1991); Nelson et al., *Pharmacogenetics* 6, 1–42 (1996). Insect cells (e.g., SF9) with appropriate vectors, usually derived from baculovirus, are also suitable for expressing 2D6 and other cytochromes P450. See Luckow et al., *Bio/Technology* 6:47–55 (1988); Gonzalez et al., *Meth. Enzymol,* 206, 93–99 (1991) (incorporated by reference for all purposes). Other expression systems include yeast (Ellis et al., supra), *E. coli* (Gillam et al., *Archives Biochem. Biophys.* 319, 540–550 (1995); vaccinia virus (Gonzalez, *Pharmacol. Res.* 40, 243 (1989), and human AHH-1 lymphoblastoid cells (Crespi et al., *Carcinogenesis* 10, 295–301 (1989)).

Humans shows a wide range of 2D6 activities but are conventionally classified as extensive (EM) or poor metabolizers (PM) by the ratios of metabolized to unmetabolized drug in urine. PM individuals have a urinary metabolic ration of greater than 12.6 for debrisoquine to 4—OH-debrisoquine, of greater than 20 for sparteine to 2- and 5-dehyrdrosparteine, and greater than 0.3 for dextromethorphan/dextrophan (see Dayer et al., *Biochem. Pharmacol.* 36, 4145–4152 (1987); Schmid et al., *Clin. Pharmacol. Ther.* 38, 618–623 (1985) and Evans et al., *J. Med. Genet* 20, 321–329 (1983)). The EM phenotype is the normal phenotype. The PM phenotype occurs in about 5–10% of the population. The PM phenotype is attributable to a recessive variation in the 2D6 gene. Thus, individuals with the PM phenotype have two variant forms of the 2D6 gene in their diploid genomes, although the variant forms need not be the same. Seven different polymorphic variants of the cytochrome P450 2D6 gene have been associated with the PM phenotype. These alleles are designated 2D6A, 2D6B, 2D6C, 2D6D, 2D6E, 2D6F, and 2D6J (Gonzales & Idle, *Clin. Pharmacokinet.* 26(1), 59–70 (1994); Nelson et al., *DNA & Cell Biol.* 12(1), 1–51 (1993)). 2D6A, 2D6E and 2D6F are minor variants of the wild type gene. 2D6A has a single nucleotide deletion in exon 5 with a consequent frame shift (Kagimoto et al., *J. Biol. Chem.* 265, 17209–17214 (1990)). 2D6E and 2D6F are rare, recently described variants (Gonzales & Idle, supra). 2D6B accounts for about 70% of defective alleles. This variant has point mutations in exons 1, 3, 8 and 9 as well as a base change at the third intron splice site that results in aberrant transcript splicing (Gonzales et al., *Nature* 331, 442–446 (1988); Kagimoto et al., *J. Biol. Chem.* 265, 17209–17214 (1990)). 2D6C has a three base deletion in exon 5 (Broly and Meyer, *Pharmacogenetics* 3, 123–130 (1993)) and, on the 2D6D allele, the entire functional gene is deleted although the pseudogenes remain intact (Gaedigk et al., *Am. J. Hum. Genet.* 48, 943–950 (1991)). The 2D6J allele has base changes in both the first and ninth exons that result in amino acid changes (Yokota et al., *Pharmacogenetics* 3, 256–263 (1993)).

Several therapeutically important compounds are metabolized by 2D6. The list includes cardioactive drugs: β-blockers (bufuralol, propranolol, metoprolol, timolol) and antiarrhythmics (sparteine, encainide, flecainide, mexiletine) (Buchert & Woosley, *Pharmacogenetics* 2, 2–11 (1992); Birgersdotter et al., *Brit J. Clin. Pharmacol.* 33, 275–280 (1992)); psychoactive drugs including tricyclic antidepressants (imipramine, desipramine, nortriptyline) and antipsychotics (clozapine and haloperidol) (Dahl & Bertilsson, *Pharmacogenetics* 3, 61–70 (1993); Fischer et al., *J. Pharmacol. Exp. Ther.* 260, 1355–1360 (1992); Lerena et al., *Drug Monitor* 14, 92–97 (1992)); as well as a variety of other commonly used drugs including codeine and dextromethorphan (Eichelbaum & Gross, *Pharmac. Ther.* 46, 377–394 (1990)) as well as amphetamine, and cocaine.

III. Methods of Use

A. Identifying Compounds Metabolized by 2D6

Binding agents of the invention that inhibit enzymic activity of human cytochrome P450 2D6 can be used to assay whether compounds are metabolized by 2D6. Compounds include xenobiotics, such as a currently used and new drugs, carcinogens, pesticides or other industrial or environmental chemicals, or any endobiotic, such as a steroid hormone. The assay can indicate not only that a compound is metabolized by 2D6 but also the contribution of 2D6 to metabolizing the compound relative to other cytochromes P450 present in microsomes or cell homogenates.

Assays are performed by contacting a compound under test with human cytochrome P450 2D6 in reaction mixtures containing varying amounts of a binding agent of the invention. For example, two separate reactions may be set up, one in which the binding agent of the invention is present, and the other, a control in which the binding agent is absent. The human cytochrome P450 is often present as a microsomal extract from human or animal cells or cell lines or an extract from cell cultures expressing a collection of recombinant P450s including 2D6. The assay is performed under conditions in which 2D6 is known to be active on known substrates, such as bufurolol (see Examples). Metabolism of the compound under test is then followed from the disappearance of the compound or appearance of a metabolic product of the compound as a function of time (e.g., nmol productisec). See, e.g., Buters et al., *Drug Metab. Dispos.* 22, 688 (1994). The metabolism of the compound is analyzed as a function of the amount of binding agent present. If the metabolism quantitatively decreases with amount of binding agent, it can be concluded that 2D6 metabolizes the compound.

The percentage inhibition of 2D6 metabolism of a test compound may reflect both the inherent efficiency of a binding agent in blocking 2D6 activity and the contribution of cytochromes P450 other than 2D6 in metabolizing the compound. The inherent blocking efficiency of a binding agent can be determined by measuring inhibition of metabolism in a reaction mixture in which only 2D6 is present, or alternatively, in a reaction mixture in which a collection of cytochromes P450 are present but the substrate is known to be metabolized only by 2D6. Comparison of the percentage inhibition determined in these circumstances with the percentage inhibition of metabolism of a test substrate when a mixture of cytochromes P450 are present indicates the relative contributions of 2D6 and other enzymes in the mixture to metabolism of the test substrate. For example, if metabolism of a control substrate by pure 2D6 is inhibited by a binding agent by 90% and metabolism of a test substrate by a mixture of cytochromes P450 including 2D6 is inhibited 45%, it can be concluded that in the mixture, 2D6 contributes about 45/90=50% of metabolizing activity on the test substrate. Binding agents having a high degree of inhibition (e.g., at least about 90%) of a known substrate are particularly effective for quantitative analysis as described above.

Information made available by the above methods can be exploited in a number of applications. Drugs determined to be processed by 2D6 should in general not be prescribed to patients with PM phenotypes, or should be prescribed in reduced amounts or with close monitoring. Particular caution is needed in combination therapies involving two drugs metabolized by the 2D6 pathways. The information can also be valuable in drug design and screening. That is drugs can be designed or screened such that they are metabolized to a significant extent by several P450 enzymes, and are not therefore likely to cause side effects in those deficient in any single enzymes. Recognition that a carcinogen or other environmental toxin is deactivated by 2D6 signals that poor metabolizers are at particular risk from the carcinogen or compound. Conversely, recognition that a carcinogen or other environmental toxin is activated to harmful form by 2D6 indicates that poor metabolizers are less prone to harm from exposure to such a compound relative to extensive metabolizers.

B. Use of Agents for Diagnosing PM Phenotype

The binding agents are useful diagnostics to determine a patient's metabolic profile prior to treatment with a drug known or suspected to be metabolized by 2D6. Patients identified as 2D6 poor metabolizers can be given alternative therapy, a lower dosage or additional monitoring to avoid damaging side effects from their PM phenotype. Diagnosis can be performed by two assays, which are described in turn.

1. Binding Assay

Binding agents of the invention are useful for the quantitative measurement of the amount of individual P450 proteins in a sample, which may contain multiple forms of other P450 proteins. Binding between binding agent and cytochrome P450 2D6 in the sample can be detected by radioimmunoassay, ELISA or immuno blotting (see Harlow and Lane, supra). The type of immunoassay can be tailored to the particular application. In radioimmunoassay, the binding agent of the invention is typically labelled. In ELISA, the binding agent is typically unlabelled and detected using a secondary labelled reagent with affinity for the binding agent (e.g., anti-IgG $^{35}$S-or $^3$H-labeled MAb). Immuno blots are particularly useful for screening a sample with a panel of antibodies to different cytochromes P450.

2. Inhibition Assay

In an inhibition assay, the presence or absence of 2D6 in a tissue sample from a patient is determined from the capacity of a binding agent of the invention to inhibit metabolism of a known substrate of 2D6 by the tissue sample. A series of reaction mixtures are prepared each of which contains an aliquot of tissue sample from a patient being diagnosed and a known substrate of 2D6 (e.g., bufurolol). The tissue sample can be obtained from any tissue in which 2D6 is normally expressed, such as the liver. The reaction mixtures differ in the amount of binding agent of the invention present, and a control is usually included in which no binding agent is present. The binding agent used should be one that is known to inhibit 2D6 metabolism. The reaction conditions are such that the known substrate is metabolized to a detectable extent in the control if the tissue sample is from an extensive metabolizer. The rate of substrate metabolism is determined in the reaction mixtures and analyzed as a function of amount of binding agent present. If the tissue sample is from an extensive metabolizer, extensive metabolic activity should be observed in the control in which no inhibitor is present, and decreasing activity should be observed in other reaction mixtures as the amount of binding agent is increased. Conversely, if the sample is from a poor metabolizer, only background metabolic activity (attributable mainly to metabolism of the substrate by other cytochromes P450) is observed in the control, and similar levels of activity are observed in the other reaction mixtures. The lack of correlation between metabolism of substrate and amount of binding agent present signals that the tissue sample is from a poor metabolizer.

C. Other Uses

The binding agents of the invention can also be used for affinity purification of cytochrome P450 2D6. The basic procedure for affinity purification requires only one or two steps and can yield highly purified milligram quantities of cytochrome P450 2D6. For example, the binding agent can be covalently bound to Sepharose™, which is made into the form of either column or a slurry for batch purification. A sample containing cytochrome P450 2D6 is them passed through the column or slurry and binds to the binding agent-linked Sepharose™. The nonbound material containing unrelated proteins and cytochromes P450 other than 2D6 are thoroughly eluted leaving the cytochrome P450 2D6, which can then be eluted and used for a variety of chemical and physical studies. See, e.g., Cheng et al., *J. Biol. Chem.* 259, 12279–12284 (1948).

Monoclonal antibody based immunohistochemical methods can be applied to localize and examine the distribution cytochrome P450 2D6 after different inducer administration, during various physiological states related to nutrition, age, and sex, and in different species and tissues. Furthermore, the intracellular distribution of the cytochrome P450 2D6 can be determined in a way not possible by standard biochemical methods which generally cannot identify the presence of specific forms of cytochrome P450 proteins in isolated tissues and organelles. See, e.g., Gelboin, *Pharmacol. Rev.* 45, 413–453 (1993).

EXAMPLES

Materials and Methods

Human P450 2D6 was cloned (Gonzalez, et al., 1988, supra) and the cDNA was inserted into a baculovirus vector (Gonzalez, et al., *Methods Enzymol.* 206, 93–99 (1991)). Hi-Five insect cells or *Spondoptera frugipedra* (Sf9) cells were infected with the recombinant baculovirus containing the human P450 2D6 cDNA and the P450 2D6 was expressed. Cell pellets were pooled and diluted 1:2 with buffer A (0.1 M KPl pH 7.4, 20% glycerol, 1 mM EDTA, 0.35 mM DTT, 0.4 mM AEBSF, and 2 µM Leupetin), sonicated gently on ice until >95% of the cells were disrupted, as assessed by using a hemocytometer with a microscope. Protein concentrations after sonication of cells were 10–15 mg/ml (BCA method; Pierce Chemical Co., Rockford, Ill.). The cell suspension was centrifuged in a Beckman ultracentrifuge (model L5-75: T145 rotor: Beckman Instrument Co., Palo Alto, Calif.). The resulting pellet containing the hemoprotein were resuspended by homogenization in buffer A to a protein concentration of 4 mg/ml. Sodium cholate was added to a final concentration of 1% and the suspension was stirred at 4° C. for 2.5 hours. The suspension was again centrifuged for 60 mins. at 40,000 rpm which resulted in a clear supernatant containing the hemoprotein. This material was dialyzed against 4 vol. of buffer A containing no sodium cholate. For immunization the extract was injected directly as immunogen into Balb/c mice, with an approximate content of 10 µg of P450 per injection. Three mice were injected once a week for 3 weeks and their spleens removed on the 3rd day after the last injection. Serum was obtained after the 2nd injection at which time an immune response was detected. A different immunization with the same protocol was performed with purified human 2D6 obtained from the baculovirus expression system.

After fusion the cells were plated at $1 \times 10^5$/well into 96-well tissue culture plates. The supernatant from the hybridoma culture was screened with an ELISA for the presence of antibodies using a baculovirus expression extract. As controls for the specificity of the antibodies, the hybrids were also tested by ELISA with the expression extract from wild type virus (no P450). Positives to wild type material were considered non-specific and discarded. Hybridomas producing antibodies positive to expressed 2D6 and negative to expressed wild type (by ELISA) were cloned and further investigated. Hybridomas of interest were cloned at least two times at a cell density of 0.5 cell/well in 96-well tissue culture plates. Ascites fluid was produced using cells from the second cloning in mice as previously described (Gelboin et. al., *Biochemical Pharmacol.* 50, 1841–1850 (1995)) and used to test Mab inhibitory activity toward P450 2D6. Culture fluid was used for ELISA and Immunoblot (IB) studies.

ELISA (Enzyme-Linked Immunosorbent Assay) Indirect ELISA was used for testing the reactivity of hybridoma supernatants and to study their binding activity. See Gelboin et al., *Pharmacol. Rev.* 45, 413–453 (1993) and Gelboin et al., (1995) supra) The assay was performed by standard methods using alkaline phosphatase-conjugated goat F(ab')2 fragment to mouse IgG (γ chain specific) or to mouse IgM (µ chain specific) from Jackson Immuno-Research Laboratories. The antigens for coating polystyrene flat bottom immunoassay plates were as follows: (a) partially purified lysate of insect cells infected with either wild type baculovirus or expressing P450 h2D6 (pmol/well); (b) lysates of Hep G2 cells infected with the wild type or recombinant vaccinia virus P450 expressing systems (5 pmol/well).

Immunoblot Assay—(Gelboin et al., (1995) supra)P450s expressed from baculovirus (1A1, 2D6, 2E1, 3A4, 2B6) or vaccinia viruses human P450s 1A2, 2B6, 2D6, 2E1, 3A4, 3A5, 2C9, 2C8 and rat P450s mouse 1A1, 1A2, rat 2A1, and rabbit 4B1, respectively, and liver microsomes were used for the IB. Proteins were separated by electrophoresis on SDS-PAGE gels, transferred onto nitrocellulose filters, and probed with MAbs from either cell culture or ascites fluid. MAb binding was detected using alkaline phosphatase-conjugated goat F(ab')2 anti-mouse IgG (γ chain specific) or to mouse IgM (µ chain specific).

MAb Inhibition of Human P450 2D6 Catalyzed Bufarolol Metabolism—Ascites containing—MAbs at a ascites protein concentration ranging from 10 to 500 µg were preincubated with 10–50 pmol of human P450 2D6, microsomes expressed in lymphoblast cells in 100 µl, of 50 mM potassium phosphate buffer (pH 7.4) at 37° C. for 5 min, and the mixture was diluted with potassium phosphate buffer to 0.97 mL. Bufurolol (50 µM) or phenanthrene (200 µM) and NADPH (1 mM) were added to a final volume of 1.0 mL to initiate the reaction. A MAb made against unrelated egg white lysozyme was used as a negative control. For cross-reactivity studies phenanthrene was used as substrate for all the P450s tested (Gelboin et. al., *Biochem. Pharmacol.* 50,1841–1850 (1995); *Chem. Res. Toxicol.* 9, 1023–1030 (1996)).

High Performance Liquid Chromatography—The HPLC was performed on a Hewlett-Packard Model HP 1050 liquid chromatograph equipped with an HP Model 1050 autosampler, a ternary solvent delivery system, and a multiple-wavelength detector, controlled by a Hewlett Packard $HPLC^{2D}$ Chemstation software and a Compaq Prolinea 4/66 personal computer.

RESULTS

About 700 hybridomas were formed from the fusion of myeloma cells with spleen cells from mice immunized with extracts or purified baculovirus-expressed human P450 2D6. The MAbs produced by the hybridomas were characterized for specific binding to 2D6, lack of specific binding to other human cytochromes P450 and capacity to inhibit enzymatic activity of human cytochrome P450. From the initial pool, monoclonal antibodies designated Mab 512-1-8, MAb 50-1-3, MAb 903-1-7 and MAb 252-3-4 and MAbs 4-74-1 and 4-100-3, showed useful properties. The latter two were derived by immunization with the purified P450 2D6. The six MAbs were found highly specific for human P450 2D6 as measured by their binding by ELISA (Table 1) to P450 2D6 and their non-binding to eleven other cytochromes P450 expressed from vaccinia or baculovirus vectors. The six MAbs bind strongly to human P450 2D6, and do not bind to the wild type baculo-expression extract and vaccinia expressed human P450s 1A2, 2C8, 2C9, 3A4, 3A5, 2B6, 2E1, mouse 1A2, rat 2A1, 2B1 and rabbit 4B1. Another measurement of the character of the isolated antibodies is their ability to yield an immunoblot (IB) with the human P450 2D6. The MAb 512-1-8 yielded a positive immunoblot with human P450 2D6 (Table 2). The MAb 903-1-7 and 252-3-4 exhibited a positive but weaker IB. The MAb 50-1-3 did not yield an IB with h2D6. The MAbs 4-74-1 and 4-100-3 gave very strong IBs. None of the MAbs cross reacted with human 1A1, 1A2, 2B6, 2E1 or 3A4.

TABLE 1

Cross Reactivity of Monoclonal Antibodies to Human P450 2D6 with other P450s ELISA (O.D.)

| P450** | 512-1-8* | 50-1-3* | 903-1-7* | 252-3-4* | 4-74-1+ | 4-100-3+ |
|---|---|---|---|---|---|---|
| bv Wild | 0.07 | 0.07 | 0.08 | 0.04 | 0.06 | 0.19 |
| vv Wild | 0.05 | 0.05 | 0.07 | 0.06 | 0.05 | 0.13 |
| bv h2D6 | 1.38 | 0.95 | 1.16 | 1.47 | 0.86 | 0.93 |
| h2D6mics** | 0.46 | 0.31 | 0.31 | 0.4 | 0.33 | n.d. |
| h2D6* | 0.54 | 0.04 | 0.05 | 0.04 | 2.00 | n.d. |
| h1A2 | 0.04 | 0.04 | 0.05 | 0.05 | 0.05 | 0.11 |
| h2B6 | 0.05 | 0.04 | 0.05 | 0.05 | 0.07 | 0.09 |
| h2C8 | 0.04 | 0.03 | 0.05 | 0.05 | 0.05 | 0.06 |
| h2C9 | 0.065 | 0.03 | 0.06 | 0.05 | 0.05 | 0.07 |
| h2C9 | 0.07 | 0.04 | 0.06 | 0.06 | 0.05 | 0.08 |
| h2E1 | 0.08 | 0.05 | 0.06 | 0.05 | 0.06 | 0.09 |
| h3A4 | 0.05 | 0.05 | 0.06 | 0.05 | 0.06 | 0.1 |
| h3A5 | 0.06 | 0.05 | 0.07 | 0.06 | 0.06 | 0.1 |
| m1A1 | 0.05 | 0.03 | 0.05 | 0.05 | 0.04 | 0.07 |
| m1A2 | 0.04 | 0.02 | 0.03 | 0.04 | 0.04 | 0.06 |
| r2A1 | 0.05 | 0.03 | 0.04 | 0.04 | 0.05 | 0.09 |
| r2B1 | 0.06 | 0.04 | 0.05 | 0.05 | 0.06 | 0.09 |
| r4B1 | 0.05 | 0.04 | 0.05 | 0.05 | 0.06 | 0.11 |
| Isotype | IgG | IgG | IgM | IgG | IgG | IgG |

All P450s except 2D6 were vaccinia expressed
All P450s are vaccinia expressed except where noted as bv
n.d. = not determined
m = mouse
r = rat
h = human
bv – baculo virus expressed
vv = vaccinia virus expressed
* = immunization with bv P450 2D6 expressed extract
+ = immunization with purified bv expressed P450 2D6
** = microsomes expressing 2D6 from Gentest Corporation

TABLE 2

Immunoblot (IB), Cross Reactivity of Monoclonal Antibodies to Human P450 2D6

| P450** | 512-1-8* | 50-1-3* | 903-1* | 252-3* | 4-74-1+ | 4-100-3+ |
|---|---|---|---|---|---|---|
| bv wild | − | − | − | − | − | − |
| bv H2D6 | ++ | − | + | + | +++ | +++ |
| 2D6 mics** | ++ | − | + | + | ++ | ++ |
| bvh2D6+ | ++ | − | n.d. | + | +++ | n.d. |
| bv h1A1 | − | − | n.d. | n.d. | − | − |
| bv h1A2 | − | − | n.d. | n.d. | n.d. | n.d. |
| bv h2B6 | − | − | n.d. | n.d. | − | − |

TABLE 2-continued

Immunoblot (IB), Cross Reactivity of Monoclonal Antibodies to Human P450 2D6

Figure 1:
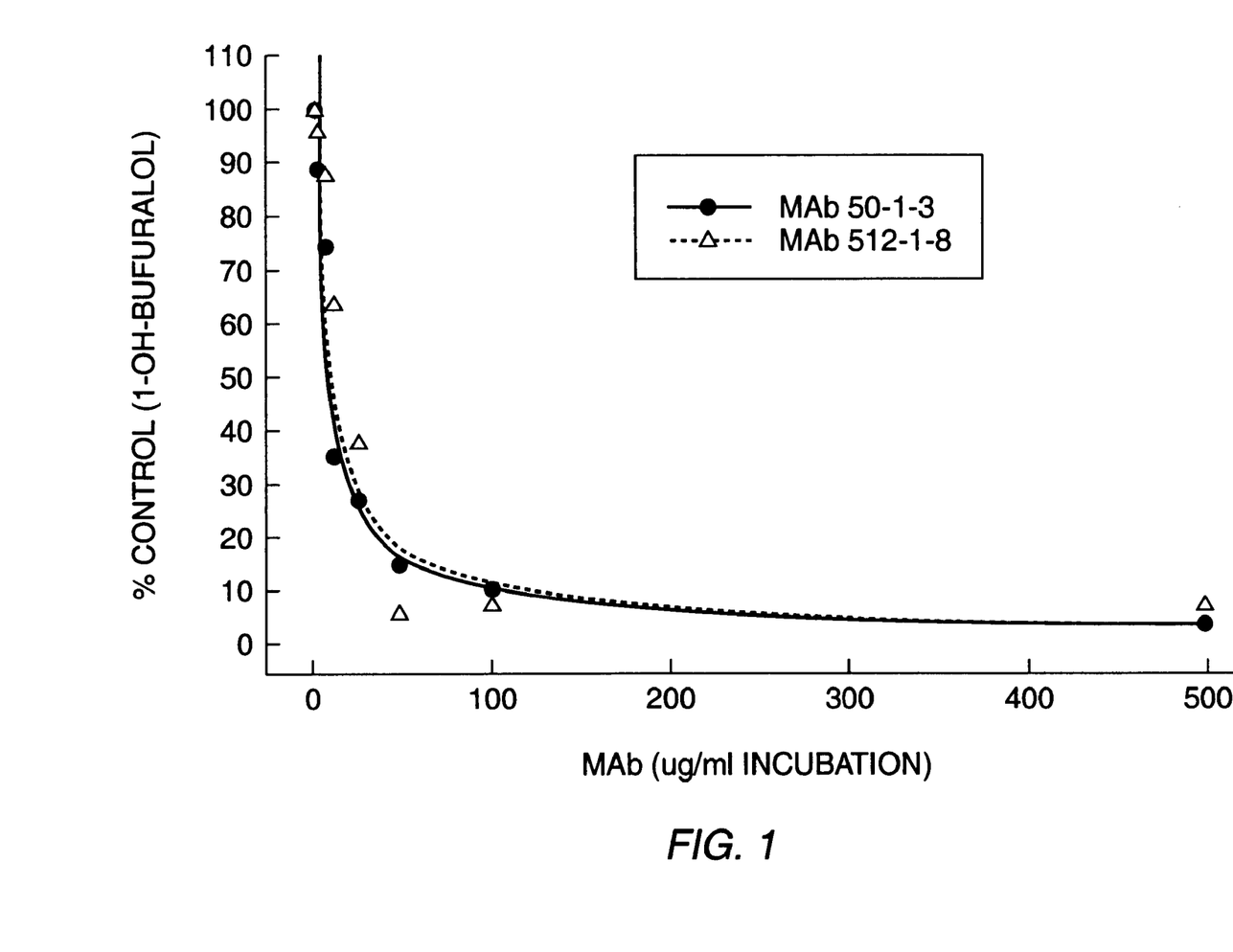
FIG. 1: Inhibitory effect of MAb 512-1-8 and 50-1-3 on Human P450 2D6 Catalyzed Bufuralol Metabolism.
Figure 2:
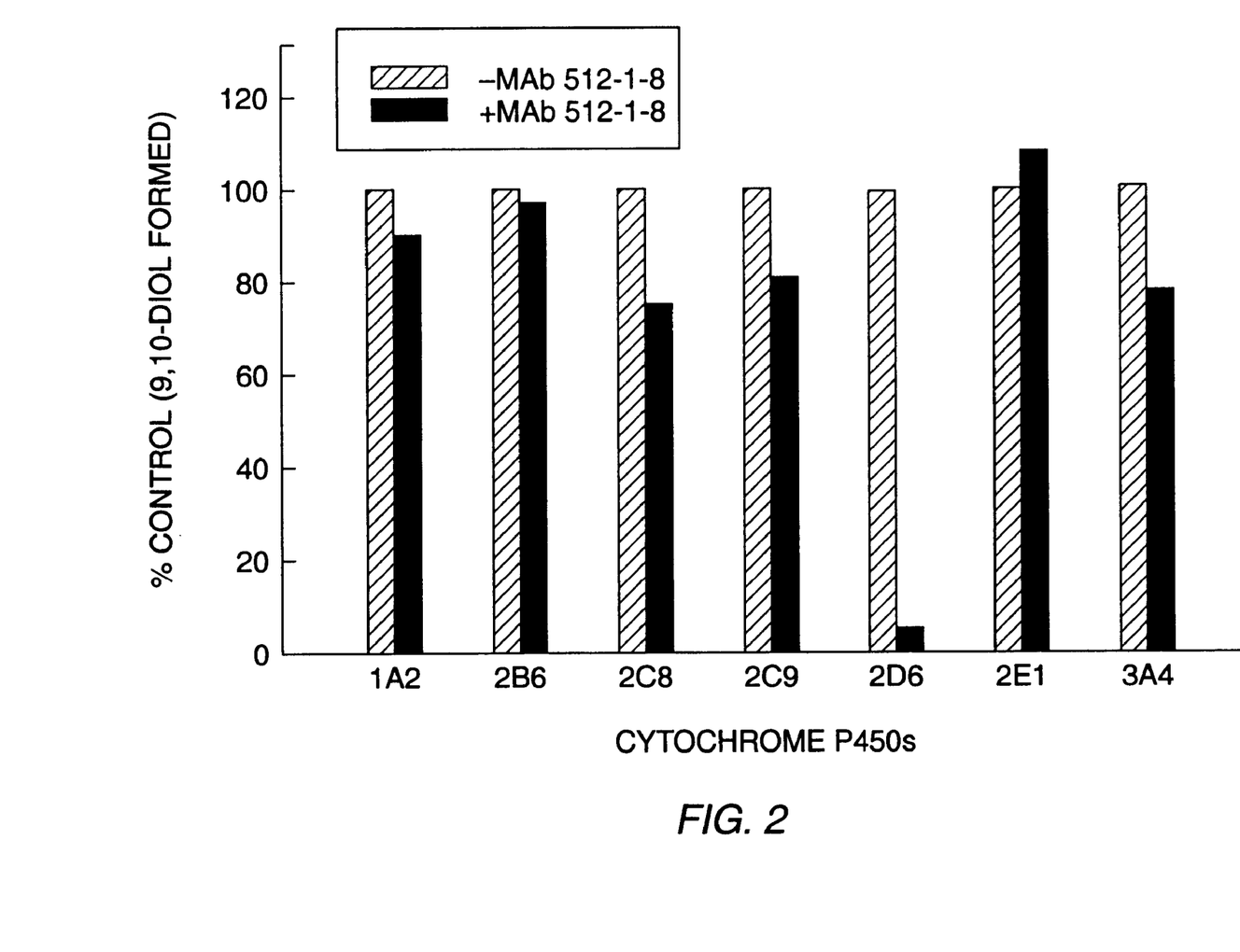
FIG. 2: Inhibitory effect of MAb 512-1-8 on P450 2D6 catalyzed phenanthrene metabolism and lack of cross reaction with other human cytochromes P450.

| P450** | 512-1-8* | 50-1-3* | 903-1* | 252-3* | 4-74-1+ | 4-100-3+ |
|---|---|---|---|---|---|---|
| bv h2E1 | − | − | n.d. | n.d. | − | − |
| bv h3A4 | − | − | n.d. | n.d. | − | − | n.d. = not determined
m = mouse
r = rat
h = human
bv – baculo virus expressed
vv = vaccinia virus expressed
* = immunization with bv P450 2D6 expressed extract
+ = immunization with purified bv expressed P450 2D6
** = microsomes expressing 2D6 from Gentest Corporation FIG. 1 shows the strong inhibitory activity of both MAb 512-1-8 and MAb 50-1-3 on human P450 2D6 enzyme activity as measured by bufurolol metabolism. The P450 2D6 catalyzed metabolism of bufurolol was inhibited by these MAbs by more than 90%. Thus, one of the MAbs, 512-1-8 exhibits both immunoblotting and the strong inhibitory activity of 90% of human P450 2D6. FIG. 2 shows the inhibitory activity of 512-1-8 was highly specific to human cytochrome P450 2D6 and showed no inhibitory effect on phenanthrene metabolism catalyzed by human P450s 1A2, 2B6, 2C8, 2C9, 2E1 and 3A4. The other monoclonal antibody 50-1-3, although showing strong P450 2D6 inhibitory activity, exhibits no immunoblot activity. The two MAbs 4-74-1 and 4-100-3 gave very strong IB with h2D6 but were not inhibitory.

Figure 3:
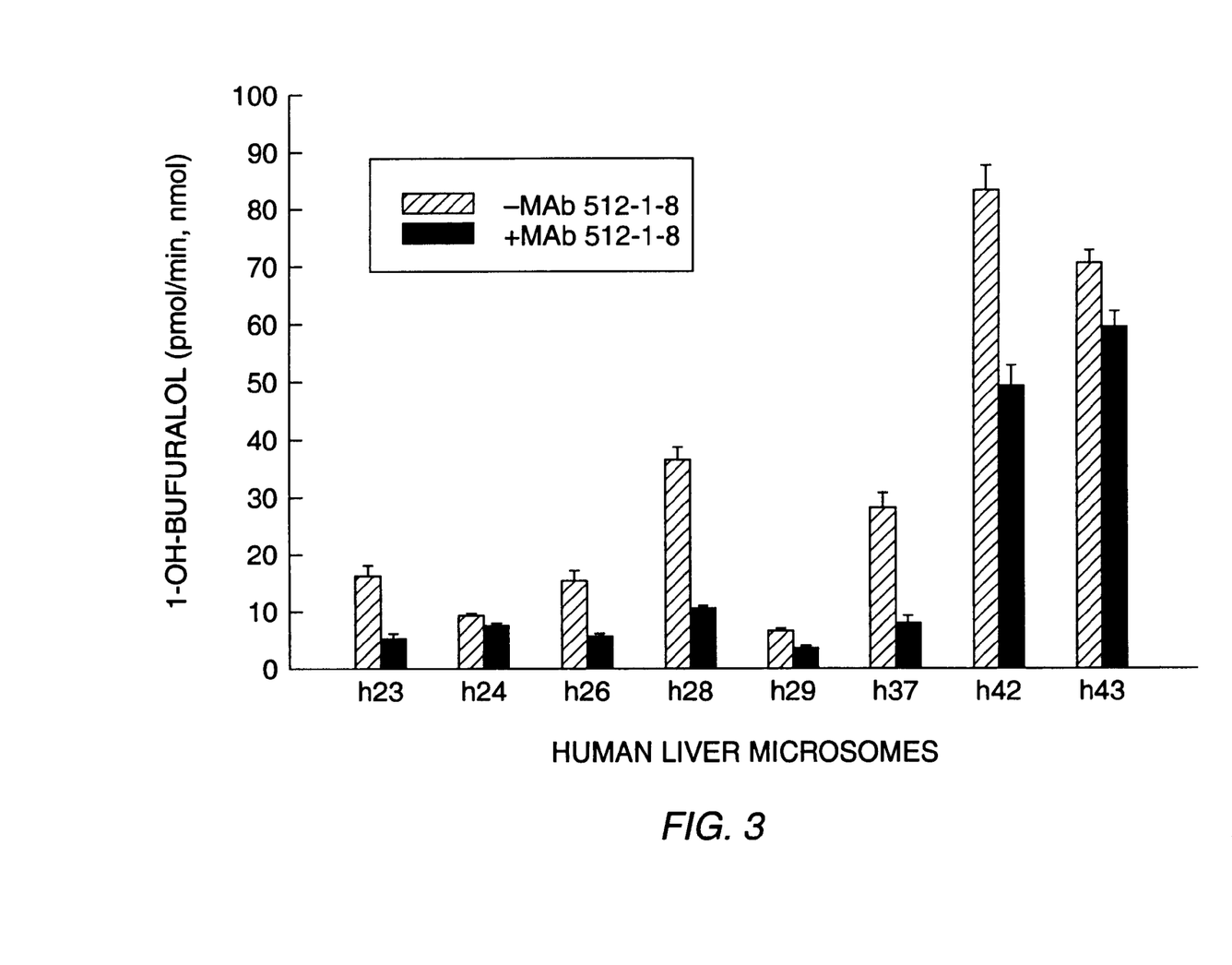
FIG. 3: Inhibitory effect of MAb 512-1-8 on bufurolol metabolism by eight human liver samples.

The inhibitory Mab 512-1-8 was used to measure the role of cytochrome P450 2D6 in the metabolism of bufarolol by human liver microsomes from different individuals. FIG. 3 shows that the amount of inhibition observed with the addition of the MAb 512-1-8 to eight different human microsome samples ranged from 20–80%. The results shows a wide variation between eight individuals and the contribution of P450 2D6 to the total metabolism of bufarolol. This ranges from 25% in sample 28 to approximately 80% in sample 43 with the other six samples intermediate between these two values. This type of analysis can be made for any substrate of P450 2D6. The MAb 512-1-8 has a unique dual purpose utility. Thus, the monoclonal antibody has properties which can be utilized to determine both the amount of cytochrome P450 2D6 protein in human tissue, and in the presence of multiple P450s, determine the role of cytochrome P450 2D6 in the metabolism of clinically used drugs and drugs under development.

Although the foregoing invention has been described in detail for purposes of clarity of understanding, it will be obvious that certain modifications may be practiced within the scope of the appended claims. All publications and patent documents cited above are hereby incorporated by reference in their entirety for all purposes to the same extent as if each were so individually denoted.

What is claimed is:

1. A monoclonal antibody that competes with a monoclonal antibody selected from the group consisting of MAb 512-1-8 (ATCC HB12266), and MAb 50-1-3 (ATCC HB-12267) for specific binding to human cytochrome p450 2D6 and specifically inhibits catalyzed metabolism of bufuralol human cytochrome P450 2D6 by at least 75%, wherein the monoclonal antibody of comprises a light chain variable domain having at least 80% sequence identity with the light chain variable domain of a monoclonal antibody selected from the group consisting of MAb 512-1-8 (ATCC HB-12266), and MAb 50-1-3 (ATCC HB-12267), the percentage sequence identity of the light chains being determined by alignment of amino acids by Kabat numbering; and a heavy chain variable domain having at least 80% sequence identity with the heavy chain variable domain of a monoclonal antibody selected from the group consisting of MAb 512-1-8 (ATCC HB-12266), and MAb 50-1-3 (ATCC HB-12267) the percentage sequence identity of the heavy chains being determined by alignment of amino acids by Kabat numbering.

2. A monoclonal antibody that competes with a monoclonal antibody from the group consisting of MAb 512-1-8 (ATCC HB-12266), and MAb 50-1-3 (ATCC HB-12267) for specific binding to human cytochrome p450 2D6 and specifically inhibits catalyzed metabolism of bufuralol human cytochrome P450 2D6 by at least 75%, wherein the monoclonal antibody comprises a light chain variable domain comprising three CDR regions from the light chain of a monoclonal antibody selected from the group consisting of MAb 512-1-8 (ATCC HB-12266) and Mab 50-1-3 (ATCC HB-12267), and a heavy chain variable domain comprising three CDR regions from the heavy chain of a monoclonal antibody selected from the group consisting of MAb 512-1-8 (ATCC HB-12266) and MAb 50-1-3 (ATCC HB-12267).

3. The monoclonal antibody of claim 1 or 2 that lacks specific binding to at least one cytochrome P450 selected from the group consisting of human cytochromes P450 1A2, 2C8, 2C9, 3A4, 3A5, 2B6, and 2E1.

4. The monoclonal antibody of claim 1 or 2 that lacks specific binding to each of human cytochromes P450 1A2, 2C8, 2C9, 3A4, 3A5, 2B6, and 2E1.

5. The monoclonal antibody of claim 1 or 2 that inhibits human cytochrome P450 2D6-catalyzed metabolism of bufuralol by at least 90%.

6. The monoclonal antibody of claim 1 or 2 that competes with MAb 50-1-3 for specific binding to human cytochrome p450 2D6 and binds to a conformational epitope of human cytochrome P450 2D6.

7. The monoclonal antibody of claim 1 or 2 that competes with MAb 512-1-8 for specific binding to human cytochrome P450 2D6 and binds to a nonconformational epitope of human cytochrome P450 2D6.

8. The monoclonal antibody of claim 1 or 2 that is a Fab fragment.

9. The monoclonal antibody of claim 1 or 2 that is a mouse antibody.

10. The monoclonal antibody of claim 1 or 2 selected from the group consisting of MAb 512-1-8 and MAb 50-1-3.

11. A cell line producing the monoclonal antibody of claim 10.

12. The cell line of claim 11 that is a eucaryotic cell line.

13. The cell line of claim 11 that is a procaryotic cell line.

14. A monoclonal antibody that binds to the same epitope as a monoclonal antibody selected from the group consisting of MAb 512-1-8 (ATCC HB-12266), and MAb 50-1-3 (ATCC HB-12267) and specifically inhibits catalyzed metabolism of bufuralol human cytochrome P450 2D6 by at least 75%.

15. A monoclonal antibody designated MAb 4-74-1 (ATCC HB-12268) or a binding fragment thereof.

16. A cell line producing the antibody of claim 15.

17. A method of determining whether cytochrome P450 2D6 metabolizes a compound, comprising:

contacting the compound with cytochrome P450 2D6 in the presence of varying amounts of a monoclonal antibody as defined by claim 1 or 14; and assaying metabolism of the compound as a finction of amount of monoclonal antibody, a decrease of metabolism with increasing amount of monoclonal antibody indicating that cytochrome P450 2D6 metabolizes the compound.

18. The method of claim 17, wherein the compound is contacted with cytochrome P450 2D6 in a sample containing a collection of cytochrome P450 enzymes including 2D6.

19. The method of claim 18, wherein the sample is a tissue sample.

20. The method of claim 19, wherein the collection of enzymes are obtained from a cell culture expressing the enzymes.

21. The method of claim 20, wherein the compound is a drug, steroid or carcinogen.

22. A method of detecting cytochrome p450 2D6, comprising:

contacting a sample suspected of containing cytochrome P450; 2D6 with a a monoclonal antibody as defined by any of claims 1, 15 or 14; and determining whether the monoclonal antibody specifically binds to the sample, specific binding indicating the presence of cytochrome P450 2D6 in the sample.

* * * * *